(12) United States Patent
Fodor et al.

(10) Patent No.: US 11,266,763 B2
(45) Date of Patent: Mar. 8, 2022

(54) METHOD AND DEVICE FOR IN VIVO BRONCHUS REGENERATION

(71) Applicant: Biostage, Inc., Holliston, MA (US)

(72) Inventors: William Fodor, Holliston, MA (US); Linghui Meng, Holliston, MA (US); Sherif Soliman, Holliston, MA (US); Shunfu Hu, Holliston, MA (US)

(73) Assignee: Biostage, Inc., Holliston, MA (US)

( * ) Notice: Subject to any disclaimer, the term of this patent is extended or adjusted under 35 U.S.C. 154(b) by 0 days.

(21) Appl. No.: 16/593,250

(22) Filed: Oct. 4, 2019

(65) Prior Publication Data

US 2020/0108173 A1   Apr. 9, 2020

Related U.S. Application Data

(60) Provisional application No. 62/741,544, filed on Oct. 5, 2018, provisional application No. 62/740,962, filed on Oct. 4, 2018.

(51) Int. Cl.
| | |
|---|---|
| *A61L 27/26* | (2006.01) |
| *A61L 27/34* | (2006.01) |
| *A61L 27/36* | (2006.01) |
| *A61L 27/38* | (2006.01) |
| *A61L 27/56* | (2006.01) |

(52) U.S. Cl.
CPC ........... *A61L 27/26* (2013.01); *A61L 27/34* (2013.01); *A61L 27/3679* (2013.01); *A61L 27/3691* (2013.01); *A61L 27/3695* (2013.01); *A61L 27/3834* (2013.01); *A61L 27/3882* (2013.01); *A61L 27/56* (2013.01); *A61L 2300/412* (2013.01); *A61L 2420/06* (2013.01); *A61L 2430/34* (2013.01)

(58) Field of Classification Search
CPC ...... A61L 27/26; A61L 27/3882; A61L 27/34; A61L 27/3679; A61L 27/3691; A61L 27/3695; A61L 27/3834; A61L 27/56; A61L 2300/412; A61L 2420/06; A61L 2430/34; A61L 27/16; A61L 27/18; A61L 2430/22; A61L 2400/12

See application file for complete search history.

(56) References Cited

U.S. PATENT DOCUMENTS

| | | | | |
|---|---|---|---|---|
| 10,265,153 | B2 * | 4/2019 | La Francesca | A61L 27/3834 |
| 2014/0107803 | A1 * | 4/2014 | Grosse | C12M 25/14 |
| | | | | 623/23.72 |
| 2015/0086607 | A1 | 3/2015 | Johnson et al. | |

(Continued)

FOREIGN PATENT DOCUMENTS

| | | |
|---|---|---|
| WO | 2015153011 A1 | 10/2015 |
| WO | 2017083838 A1 | 5/2017 |

OTHER PUBLICATIONS

International Search Report and Written Opinion, International Application No. PCT/US2019/054694, dated Jan. 16, 2020, 12 pages.

(Continued)

*Primary Examiner* — Quanglong N Truong
(74) *Attorney, Agent, or Firm* — Young Basile Hanlon & MacFarlane, P.C.

(57) ABSTRACT

Aspects of the disclosure relate methods and synthetic scaffolds for regenerating hallow organs present in the respiratory system such as bronchus tissue.

18 Claims, 16 Drawing Sheets

(56) References Cited

U.S. PATENT DOCUMENTS

2017/0151049 A1\* 6/2017 La Francesca ........... A61F 2/04
2020/0114045 A1\* 4/2020 Meng .................. A61L 27/3882

OTHER PUBLICATIONS

International Preliminary Report on Patentability and Written Opinion of the International Searching Authority for International Application No. PCT/US2019/054694, issued by the International Bureau of WIPO, dated Mar. 23, 2021, 7 pages.

\* cited by examiner

METHOD AND DEVICE FOR IN VIVO BRONCHUS REGENERATION

CROSS-REFERENCE TO RELATED APPLICATIONS

U.S. Provisional Patent Application Ser. No. 62/741,544, filed on Oct. 5, 2018, and 62/740,962, filed Oct. 4, 2018, the entire disclosure of which is hereby incorporated by reference.

FIELD

This application pertains to synthetic cell delivery devices that promote and/or accomplish in vivo tissue regeneration at or proximate to bronchial anastomoses.

BACKGROUND

Pneumonectomy is well known for a high risk of postoperative death for the management of non-small cell lung cancer and it is also associated with an increased risk of long-term cardiopulmonary complications, with a negative influence on quality of life and long-term survival. To avoid the complications of pneumonectomy, sleeve lobectomy has emerged as the preferred operation in case of central non-small cell lung cancer because it has the advantage of preserving the pulmonary parenchyma and consequently offers better quality of life. However, the use of this technique is sometimes unfeasible in cases of large bronchial involvement because the bronchial ends are too remote to perform a safe tension-free anastomosis. Moreover, the sleeve lobectomy is suspected of a higher rate of local recurrence of cancerous cells. Its elective use could offer a more anatomic regeneration/reconstruction of the airway. It would permit longer inclusion times of the organ resections with better security margins and, thus, reducing the risk of locoregional recurrence and the necessity to perform a pneumonectomy.

Disclosed herein is a method and device addressing or eliminating one or more issues and complications that can arise during procedures including but not limited to sleeve lobectomies.

Thus, there is a need for a bronchial substitute that would be clinically advantageous to facilitate resections thereof of hollow organs, like those in the pulmonary system. There is a need for a bronchial substitute that can completely replace the damaged portion of the hollow organ and allow full reconstruction of the damaged area. There is a need for a method that allows endoscopic insertion of the substitute that ultimately leads to complete removal of the substitute so that guided tissue growth of the damaged hollow organ completely reconstructs the damaged localized area.

SUMMARY

The synthetic scaffold containing a spun polymeric fiber provides an endoscopic delivery system for a permanent cellular bridge that reconstructs the airway so that the damaged anastomosis is completely restored without having to move either end of the trachea axially. The synthetic scaffold containing a spun polymeric fiber further provides a means to propagate adipose tissue that diffuses from the spun polymeric fiber to the ends of the resected trachea so that the synthetic scaffold is removable with minimal or no remaining cellular tissue, electrospun fiber, or both. The present teachings further provide a method for synthesizing a scaffold with an electrospun fiber and autologous or allogenic cells that is endoscopically inserted into the pulmonary tract, create a permanent organic bridge that promotes guided tissue growth so that the synthetic scaffold is removable without cellular material, and the electrospun fiber is removable or bioabsorbable.

In certain embodiments, the synthetic scaffold includes a body section and at least one colonized cell line. The body section has a first end and a second end opposed to the first end and can at least one portion that is configured as tubular. The body section also has an outwardly oriented surface that has at least one region that is composed of spun polymeric fibers having an average fiber diameter between 15 nm and 10 microns. At least a portion of the spun polymeric fiber is interlinked to form ports having an average opening area that is less than 50 microns, the pores defining at least one porous region present on the outwardly oriented surface. The at least one colonized cell unit adheres to the porous region defined on the outwardly oriented face of the body section.

Also disclosed in a method for addressing and treating trauma in the hollow organs present in the respiratory system of a subject that includes the steps of resecting a portion of a tubular organ in the respiratory system of a subject that produces a resected hollow organ portion in which the resected hollow organ portion remaining in the subject. The method also includes the step of implanting a synthetic scaffold at the site of resection, the synthetic scaffold including an outer polymeric surface and at least one colonized cell line adhering to the outer polymeric surface of the synthetic scaffold. The synthetic scaffold is maintained at the resection site for an interval of time sufficient to achieve guided tissue growth along the synthetic scaffold, the guided tissue growth derived from and in contact with the tissue present in the resected organ portion remaining in the subject. After achieving guided tissue growth, the synthetic scaffold is removed from the implantation site, the removal occurring in a manner such that the guided tissue growth remains in the contact with the resected portion of the tubular organ remaining in the subject.

These and other aspects of the present disclosure are disclosed in the following detailed description of the embodiments, the appended claims and the accompanying figures.

BRIEF DESCRIPTION OF THE DRAWINGS

The teachings herein are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
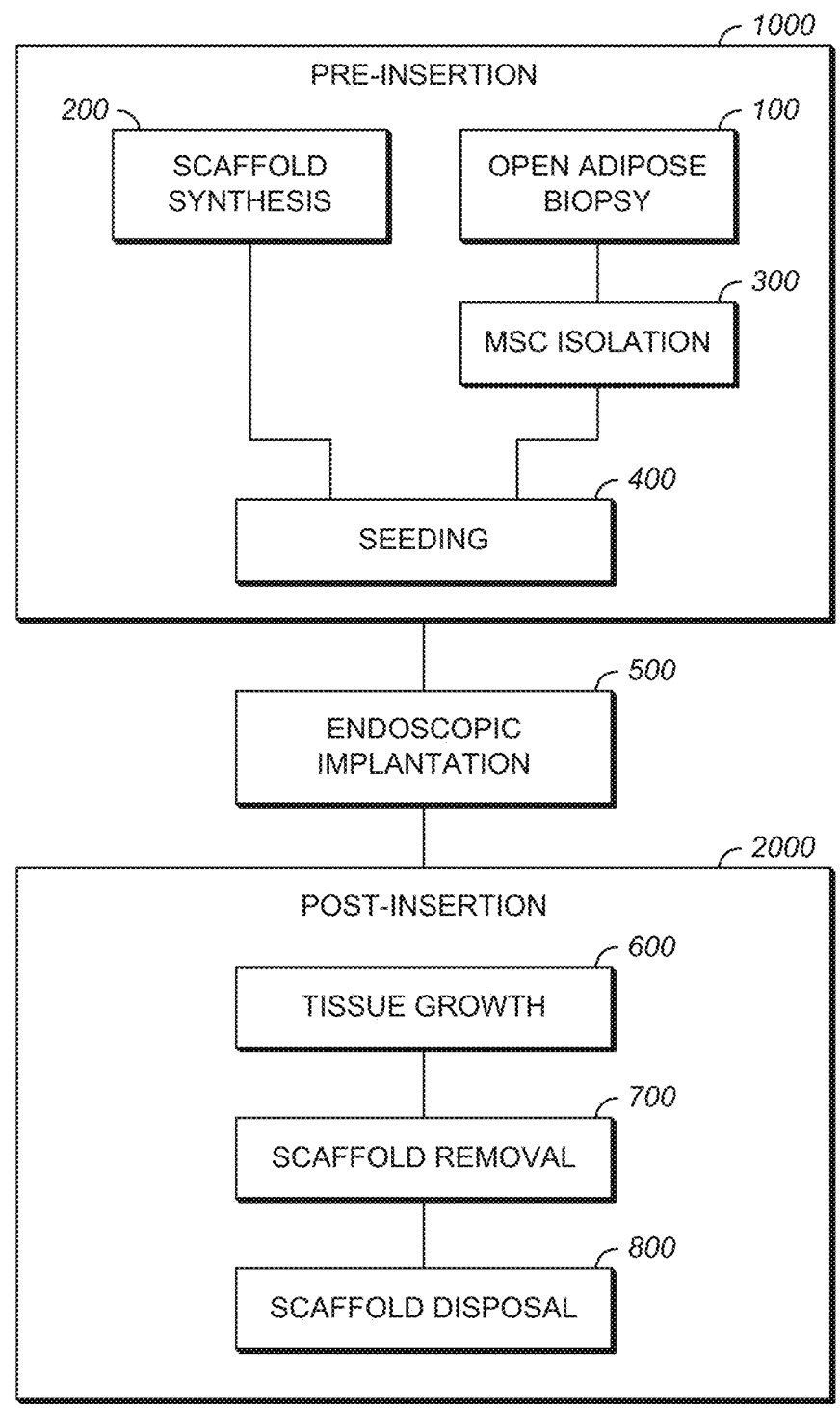
FIG. 1 is a flow chart for a method of for addressing a resection in a hollow organ in the respiratory is a flow chart for adipose biopsy, scaffold electrospinning, seeding, surgical implantation and associated characterizations according to an embodiment depicted herein.

Aspects of the disclosure relate in part to the remarkable discovery that inserting a temporary synthetic scaffold into a target region of a hollow organ present in the respiratory system of a subject can promote or enhance the regeneration of new tissue such as bronchus tissue (e.g., a complete and functional bronchus) in the subject without fully incorporating the scaffold into the regenerated tissue. In certain embodiments, the hollow organ is the bronchus. Thus, in some embodiments, the disclosure provides a method for promoting or enhancing growth of bronchus tissue, the method includes delivering to the bronchus region in the respiratory system of a subject a temporary synthetic scaffold assembly, wherein delivery of the temporary synthetic scaffold assembly results in growth of new differentiated tissue in that region of the subject bridging the anastomosis present in the subject.

In some aspects, the disclosure is based, in part, on the surprising discovery that methods described herein result in the regeneration of hollow organ tissue such as bronchus tissue comprising muscle tissue, nervous system tissue, or both.

Disclosed herein is a method and device for in vivo bronchial regeneration using a temporary synthetic scaffold assembly seeded with autologous derived cells such as adipose-derived mesenchymal stem cells (aMSCs). The temporary synthetic scaffold assembly, when implanted supports bronchial tissue regeneration after bronchial resection.

The temporary synthetic scaffold assembly includes a body section that has at least a portion configured as a tubular member. The body section has an inner surface and an opposed outer surface, at least a portion of the outer surface has a porous region defined thereon. The synthetic scaffold also includes at least one colonized cell line adhering to the porous region defined outer surface of the body section on the layer of cells overlaying the outer surface, particularly overlying at least a portion of the porous region. The cells overlying the outer surface can be derived, at least in part, from the associated patient in which the temporary synthetic scaffold assembly is removably implanted.

Also disclosed is a method for regenerating tissue at an anastomosis defined in the airway a subject such as the bronchus that includes the step of implanting the temporary synthetic scaffold assembly at a location proximate to an anastomosis defined in the bronchus such that at least one resected edges of the native bronchus is in contact with the outer surface of the temporary synthetic scaffold assembly.

In some embodiments, the temporary synthetic scaffold assembly is resorbable or dissolvable under physiological conditions (e.g., within a time period corresponding approximately to the time required for tissue regeneration). In some embodiments, at least a portion of the synthetic scaffold is resorbable or dissolvable under suitable physiological conditions.

In some embodiments, the temporary synthetic scaffold assembly is removed from the subject after the formation of a regenerated functional bronchus tissue that is connected to at least one resected edge.

In some embodiments, a scaffold is designed to be readily retrievable by having a) one or more reversible attachments that can be easier to remove than a suture, for example, to help disconnect the scaffold from the surrounding tissue after tissue regeneration; and/or b) one or more features that can be used to help retrieve the scaffold, for example, after it has been disconnected from the surrounding tissue (e.g., adjacent bronchus tissue).

Non-limiting examples of reversible attachments include mechanical mechanisms (for example hooks and loops, connectors such as stents, or other mechanical attachments that can be disconnected) and/or chemical mechanisms (for example biodegradable or absorbable attachments and/or attachments that can be selectively removed by chemical or enzymatic means). In some embodiments, absorbable staples can be used. In some embodiments, absorbable staples comprise a co-polymer of polylactide-polyglycolide for example, or any other absorbable blend of material.

In some embodiments, surgical implantation and/or retrieval of a scaffold can be performed with thoracoscopic assistance.

Non-limiting examples of structural features that can assist in the retrieval or removal of a scaffold (e.g., after it is disconnected from the surrounding bronchus tissue) include holes, indents, protrusions, or other structural features, or any combination thereof these structural features are located only on the outer surface of the scaffold. One or more of these structural features can be used to help grip or hold a tool (e.g., a grasper) that is being used to retrieve the scaffold. In some embodiments, one or more of these structural features can be located at only one end of the scaffold (e.g., the end that is proximal to the mouth of the subject). In some embodiments, one or more of these structural features can be located at both ends or throughout the length of the scaffold. In some embodiments, one or more of these structural features are located only on the outer surface of the scaffold. In some embodiments, one or more of these structural features are located only on the inner surface of the scaffold. In some embodiments, one or more of these structural features are located on both the outer and inner surfaces of the scaffold. In some embodiments, a scaffold is reinforced (e.g., is thicker and/or includes stronger material)

at or around the location of one or more structural features that are used to retrieve the scaffold.

In some embodiments, a disconnected scaffold can be removed endoscopically via the lumen of the airway leading to the bronchus. In some embodiments, a disconnected scaffold can be removed surgically.

In some embodiments, the subject has diseased (e.g., cancerous) or injured bronchus or associated lung. It is contemplated that the temporary scaffold assembly as disclosed herein can be employed in classic pneumonectomy procedures in which the diseased lung is removed as part of the treatment protocol for the given subject. In certain situations, it is possible to address the treatment issues by using procedures, such as a sleeve lobectomy. It is believed that the temporary scaffold assembly as disclosed herein can increase the situations in which sleeve lobectomy as well as other suitable procedures, such as sleeve resection, can be successfully employed.

Without being to be bound by any particular theory, synthetic scaffolds described herein promote the growth of new tissue (e.g., bronchial tissue) in a subject and, therefore, provide a therapeutic benefit to the subject.

In some embodiments, the growth of new bronchial tissue results in the formation of a functional bronchus in the subject. In some embodiments, the new bronchus tissue does not incorporate the scaffold into the regenerated bronchial walls. In some embodiments, the scaffold is designed and manufactured to be absorbable and/or readily retrievable after the bronchial tissue has regenerated. In some embodiments, the scaffold is designed to be at least partially absorbable.

In some embodiments, a synthetic scaffold has a size and shape that approximates the size and shape of a diseased, resected or injured region (e.g., bronchial region) that is being replaced.

An embodiment of the method as disclosed herein is set forth in FIG. 1. As broadly depicted, the method includes a pre-insertion phase 1000, followed by an endoscopic implantation phase 500 and a post-insertion phase 2000.

In the pre-insertion phase 1000, it is contemplated that cells suitable for seeding onto the surface of the scaffold can be obtained by a suitable method such as the open adipose biopsy as at reference numeral 100. Suitable stem cells can be isolated and expanded by a suitable method as at reference numeral 300. Scaffold synthesis can be accomplished as a reference numeral 200. In certain embodiments, a polymeric structure having electrospun nanofiber can be constructed by a suitable method. In certain embodiments, the synthesis method can be as outlined in the present disclosure. In certain embodiments the electrospun nanofiber can be one or more continuous strands of a polymeric material as outlined in this disclosure. In certain embodiments, the electro spun polymeric material can be one or more of the following: polyvinylidene fluoride, syndiotactic polystyrene, copolymer of vinylidene fluoride and hexafluoropropylene, polyvinyl alcohol, polyvinyl acetate, poly(acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly(methyl methacrylate), polyethylene terephthalate, polyurethane.

As indicated, the method also includes the step of collecting suitable stem cells as can be derived form a suitable source. In certain embodiments, the stems cells can be obtained from one or more autologous stem cell collections from an individual seeking treatment. It is also with in the purview of this disclosure that other sources of stem cells can be employed.

The obtained stem cells can be suitably treated under suitable methods of stem cell expansion to obtain a cell culture expansion to obtain a suitable population of cells for seeding on to the surface of the polymeric electrospun structure produced as at reference numeral 400. Suitable cell expansion techniques would be those known to the skilled artisan. In certain embodiments, cell expansion techniques that can provide cultures rich in mesenchymal stem cells (MSCs) such as adipose-derived mesenchymal stem cells (aMSCs).

Seeding of the suitable stem cells onto the synthesized scaffold can proceed as at reference numeral 400. In certain embodiments, the tubular scaffold can be introduced into a suitable rotating bioreactor and can be attached to a support that is capable of rotating in a bath of liquid medium that is infused with the expanded cell material located within a chamber defined in the bioreactor. Where desired or required, the rotating mechanism can include magnetic drives that allow the support along with the attached scaffold to be rotated around its longitudinal axis within the liquid bath.

The produced scaffold structure is seeded with cells such as MSCs or other stem cells by depositing cell solutions on the external scaffold surface as the polymeric tubular structure comes into contact with the liquid medium. The seeded scaffold is incubated in liquid growth media present in the liquid medium that supports cell growth as the scaffold rotates in the bath of the liquid media within a bioreactor chamber. The incubation interval can be an interval sufficient to establish at least one cellular colony adhering to the first or outer face of the polymeric tubular structure. In certain embodiments, the incubation interval and be between 24 hours and 336 hours. In certain embodiments, the incubation interval can be between 36 hours and 336 hours. In certain embodiments, the incubation interval can be between 48 hours and 336 hours. In certain embodiments, the incubation interval can be between 72 hours and 336 hours. In certain embodiments, the incubation interval can be between 96 hours and 336 hours. In certain embodiments, the incubation interval can be between 120 hours and 336 hours. In certain embodiments, the incubation interval can be between 144 hours and 336 hours. In certain embodiments, the incubation interval can be between 168 hours and 336 hours. In certain embodiments, the incubation interval can be between 36 hours and 240 hours. In certain embodiments, the incubation interval can be between 36 hours and 216 hours. In certain embodiments, the incubation interval can be between 36 hours and 192 hours. In certain embodiments, the incubation interval can be between 36 hours and 168 hours. In certain embodiments, the incubation interval can be between 72 hours and 240 hours. In certain embodiments, the incubation interval can be between 72 hours and 216 hours. In certain embodiments, the incubation interval can be between 72 hours and 192 hours. In certain embodiments, the incubation interval can be between 72 hours and 168 hours.

Subsequent to incubation, the resulting polymeric scaffold structure will have at least one colony of cells adhering to its first or outer surface. In certain embodiments the resulting construct can have a plurality of discrete colonies of cells dispersed on the outer surface of the polymeric scaffold structure. In certain embodiments, the cellular material can be present as a plurality of discrete colonies of cells in suitable biomaterial. In certain embodiments, the resulting scaffolds include a cellular sheath that is in overlying relationship to the outer surface of the polymeric scaffold structure. In certain embodiments, the cellular sheath can have a thickness sufficient to provide structural integrity to the sheath layer. The sheath layer can be continuous or discontinuous. In certain embodiments, the sheath layer can be composed of a lining that is between 1 and 100 cells thick on average. Certain embodiments can have a cell thickness between 10 and 100 calls; between 10 and 30 cells; between 20 and 30 cells; between 20 and 40 cells; between 20 and 50 cells; between 10 and 20 cells; between 30 and 50 cells; between 30 and 60 cells; between 40 and 60 cells; between 40 and 70 cells; between 70 and 90 cells.

In certain embodiments, the polymeric tubular structure can be maintained in the bioreactor for an interval after cellularization after which the structure can be employed for endoscopic implantation as at reference numeral 500.

In certain embodiments, the outer surface of the polymeric scaffold will have a porous surface area that will permit one or more cells to span the area between fibers. In certain embodiments, the surface can have a plurality of pores ranging from around 10 nm to about 100 micron in surface opening area. In certain embodiments, the pores can be irregularly shaped and defined by the overlaying and variously positioned electrospun fibers. Without being bound to any theory, it is believed that the surface structure of the polymeric tubular structure that is produce by the method as disclosed herein pore size can promote cellularization and/or cell adhesion of the at least on cell colony. It is also believed that the pore size and/or pore configuration as employed herein can prevent or reduce an immune response or other unwanted host response in the subject when the cell delivery device as disclosed herein in position. In some embodiments, pores have an average pore size of less than 50 microns, less than 40 microns, less than 30 microns, less than 20 microns or less than 10 microns (e.g., approximately 5, approximately 10, or approximately 15 microns). It is contemplated that the pore size is calculated and/or estimated using computational and/or experimental techniques (e.g., using porosimetry). However, it should be appreciated that pores of other sizes also can be present on the surface of the article.

Figure 1A:
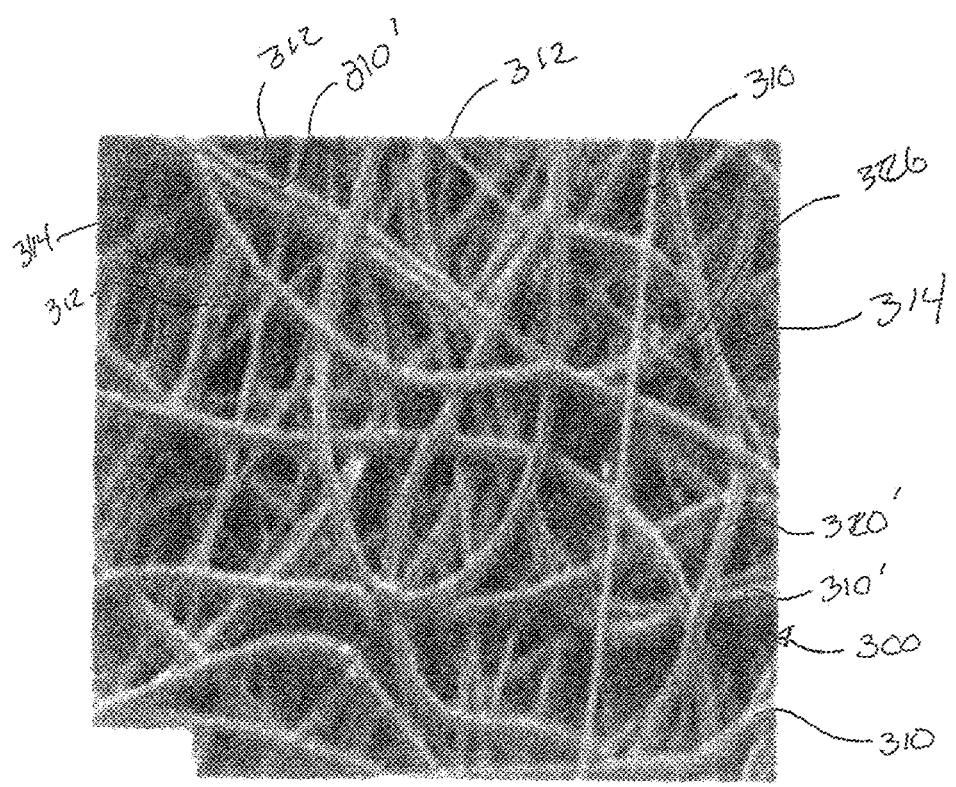
FIG. 1A is a Scanning Electron Microscopy ("SEM") of a localized surface of an embodiment of the spun surface of the body an embodiment of the of the synthetic cellular delivery device of FIG. 1C at a magnification of 1000×.

A non-limiting example of the surface of an embodiment of the polymeric tubular structure that can be synthesized by the method disclosed herein and/or can be employed in the synthetic cell delivery device and can make up at least a portion of the first face of the body of the synthetic cell delivery device as disclosed herein is presented in FIG. 1A. The embodiment of the surface presented in FIG. 1A includes a plurality of electrospun polymeric fiber sections that are in overlying fused relationship with one another. The various electrospun fiber sections include a plurality of surface-most primary fiber sections 310 that are supported and connected directly to surface-most secondary fibers sections 310' located immediately below the surface-most primary fiber sections 310. Upper intermediate fibers such as upper intermediate fiber sections 312 can be located below the surface-most secondary fiber sections 310' and can be in fused relationship with one or more of the surface-most secondary fiber sections 310'. It is to be understood that the various fibers sections, 310, 310', 312 can be composed of a continuous electrospun fiber in certain embodiments. In certain embodiments, the various fiber sections 310, 310' and 312 will overlay additional interior fiber sections in a manner that provides channels and communication through the fibers in the outer face of the polymeric tubular structure that is produced. In certain embodiments surface will have a plurality of surface pores 314 that are defined on the outermost surface. At least a portion of the pores 314 can be non-circular and include at least one angular region 326 that is define by the intersection of at least two fiber sections in certain embodiments.

Figure 11:
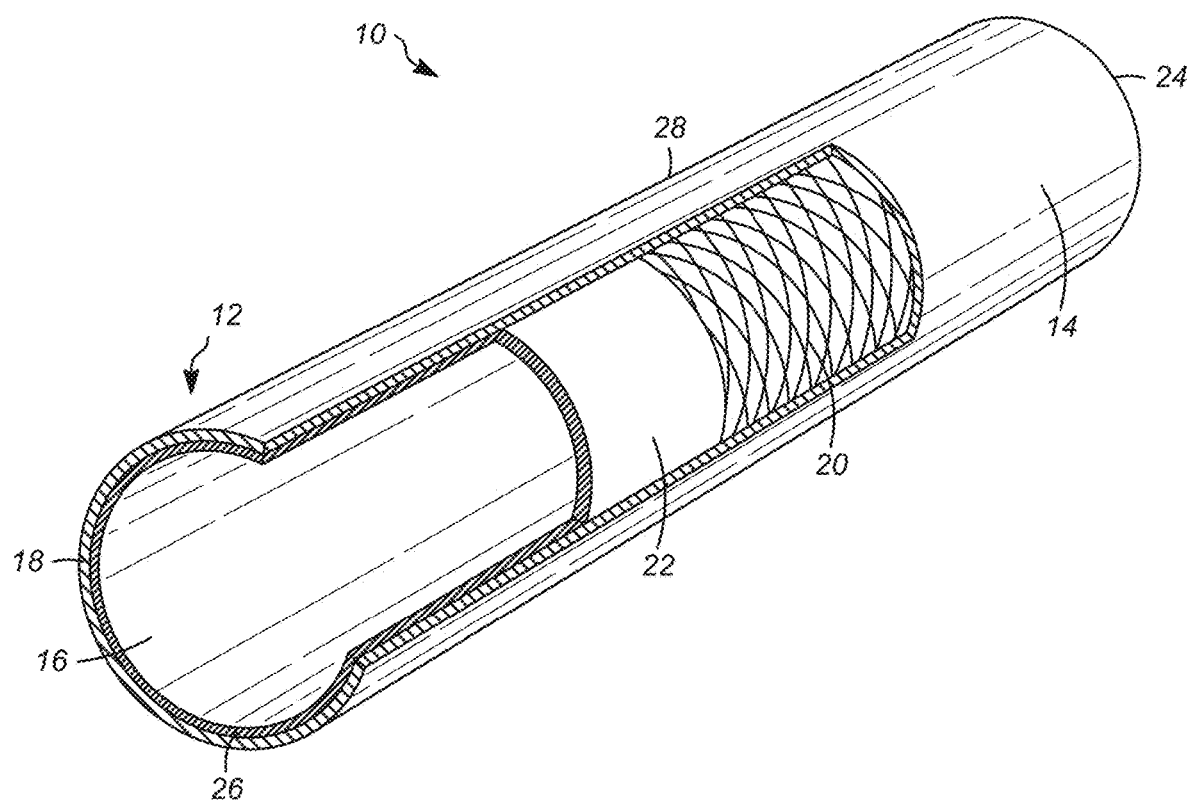
FIG. 11 is a perspective view of an embodiment of a synthetic scaffold as disclosed herein with a portion being rendered in a partial cross-section.
Figure 13:
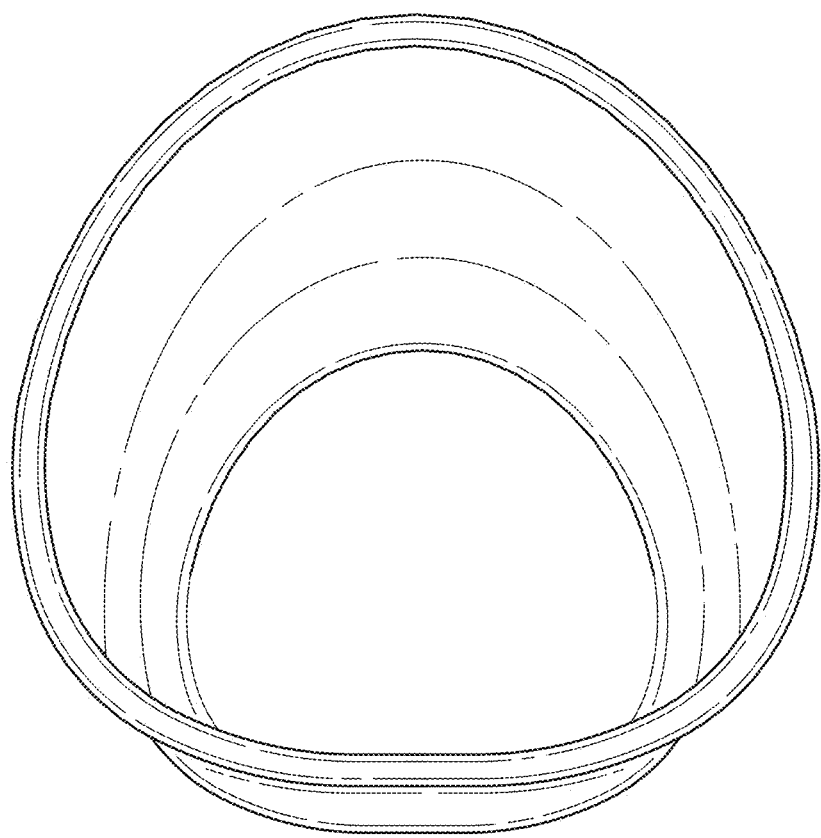
FIG. 13 a side perspective view of a second embodiment of a synthetic scaffold as disclosed herein.

In some embodiments, a scaffold will have at least two layers. The scaffold can have an approximately tubular structure in certain embodiments. FIG. 11 illustrates a non-limiting embodiment of a scaffold 10 having an approximately tubular body 12 having an interiorly oriented surface 14 and an exteriorly oriented surface 16. In some embodiments, a lateral cross-section of the scaffold 10 is approximately circular. In some embodiments, a lateral cross-section is approximately "D" shaped such as that depicted in FIG. 13. However, scaffolds 10 having other cross-sectional shapes can be used. Scaffold 10 can have any suitable length and diameter depending on the size of the corresponding tissue being regenerated. In some embodiments, a scaffold 10 can be from around 1-10 cm in length (for example 3-6 cm, e.g., about 4 cm) in certain embodiments or 1 to 3 cm long in other embodiments. However, it is contemplated that shorter or longer scaffolds 10 can be used depending on the application, needs of the patient, and/or locations in the bronchus or associated lung requiring treatment. In some embodiments, a scaffold 10 can have an inner diameter of 0.5 to 5 cm. However, scaffolds with smaller or larger inner diameters can be used depending on the application, needs of the patient, and/or locations in the bronchus requiring treatment.

In some embodiments, a scaffold 10 can be composed of a single layer of synthetic material. However, it is within the purview of this disclosure that the scaffold 10 can include more than one layer of synthetic material.

Accordingly, in some embodiments, the synthetic scaffold 10 can be composed of multiple layers (e.g., 2 or more layers, for example 2, 3, 4, 5, or more layers). In some embodiments, one or more layers are made of the same material. In some embodiments, the different layers are made of different materials (e.g., different polymers and/or different polymer arrangements). Synthetic scaffolds 10 as disclosed herein may include two or more different components that are assembled to form the scaffold as it exists (e.g., prior to cellularization and/or implantation). In some embodiments, a synthetic scaffold 10 includes two or more layers that are brought into contact with each other, for example by the synthetic techniques that are used to manufacture the scaffold 10. In some embodiments, a scaffold 10 may be synthesized using a technique that involves several steps that result in two or more layers being brought together. For example, the application of a layer of electrospun material onto a portion of the scaffold that was previously made, such as a prior layer of electrosprayed material, a prior layer of electrospun material, a surface of a different component (e.g., a braided tube or mesh) that is being incorporated into the scaffold, or a combination of two or more thereof.

In the embodiment as depicted in FIG. 11, scaffold 10 includes at least one outer layer 18 that defines the outer surface 14 of the scaffold body 12. The scaffold 10 includes at least one additional inwardly oriented layer 20. In the embodiment as illustrated, the at least one additional inwardly oriented layer 20 is in direct contact with an inwardly oriented face of the outer layer 18. Where desired or required, the at least one inwardly oriented layer 20 can be configured to provide structural support to the associated scaffold body 12. In the embodiment depicted in FIG. 11, the at least one inwardly oriented layer 20 can be configured as a suitable mesh or braid positioned circumferentially around at least a portion of the longitudinal length of the scaffold body 12. In other embodiments, it is contemplated that the at least one inwardly oriented layer 20 can be composed of a suitable polymeric layer. In the embodiment as illustrated in FIG. 11. The body 12 of scaffold 10 includes at least one layer 22 that is located interior to the mesh or braid layer 20.

Where desired or required, the scaffold 10 can have a wall thickness that is generally uniform. However, in some embodiments, the wall thickness can vary at specific regions of the body 12. In some embodiments, the wall thickness at one or both ends 24, 26 of the body 12 of scaffold 10 is different (e.g., thicker) than the walls of the central portion 28 of the scaffold 10 (not shown). In some embodiments, the thicker wall regions are stronger and provide greater support for sutures that are connected to one or both ends 24, 26 of the scaffold 10 when the scaffold is connected to surrounding bronchus tissue. The thicker wall region(s) can also include discrete configurations that facilitate suturing. Non-limiting examples of such configurations include tubes, holes, etc.

In certain embodiments, at least the exteriorly oriented surface 14 defined on the outwardly oriented layer 18 can be composed of an electrospun polymeric material. In certain embodiments, it is contemplated that the outwardly oriented wall 18 can be composed of electrospun polymeric material. In certain embodiments, the electrospun outwardly oriented layer can be in direct contact with a suitable braid material layer 20.

Fiber Orientation

Electrospun fibers can be isotropic or anisotropic. In some embodiments, fibers in different layers can have different relative orientations. In some embodiments, fibers in different layers can have substantially the same orientation. Fiber orientation can be altered in each layer of a composite or sandwich scaffold in addition.

In some embodiments, scaffolds with different porosities can be used. In some embodiments, one or more layers of a scaffold permit substantially complete cellular penetration and uniform seeding. In some embodiments, one or more layers of the scaffold may be constructed to prevent the penetration of one or more cell types, for example by densely packing the fibers. Controlling fiber diameter can be used to change scaffold porosity as the porosity scales with fiber diameter. Alternatively, blends of different polymers may be electrospun together and one polymer preferentially dissolved to increase scaffold porosity. The properties of the fibers can be controlled to optimize the fiber diameter, the fiber spacing or porosity, the morphology of each fiber, such as the porosity of the fibers or the aspect ratio and varying the shape from round to ribbon-like. In some embodiments, the mechanical properties of each fiber may be controlled or optimized, for example by changing the fiber composition, and/or the degradation rate.

Figure 12:
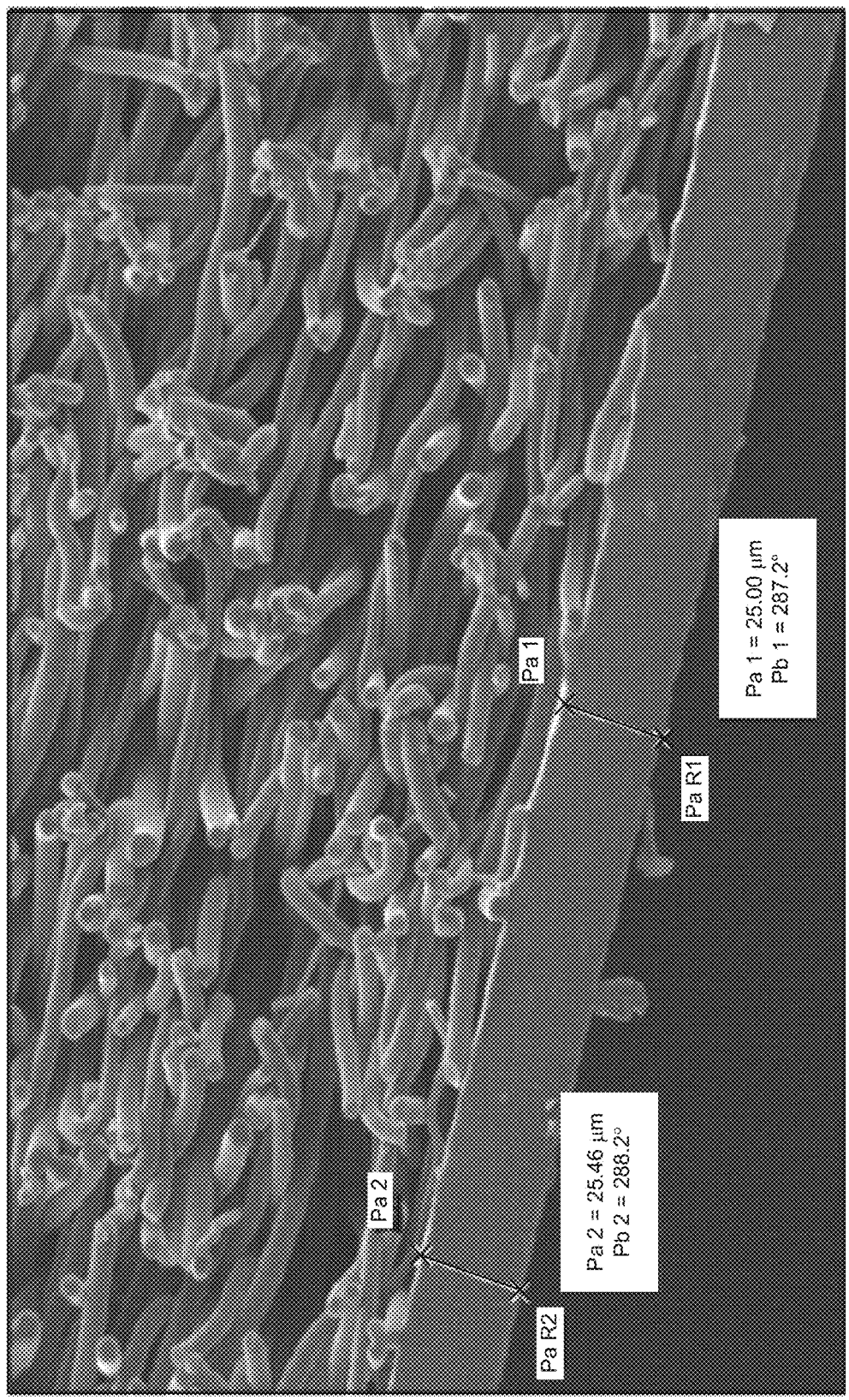
FIG. 12 is a photomicrograph of a surface of a tubing surface of an embodiment of the synthetic scaffold as disclosed herein.

In certain embodiments, the electrospun fiber material can provide a contoured surface, such as that depicted in FIG. 12. In certain embodiments, at least one electrospun layer in scaffold 10 can be a polymeric fiber material such as polycarbonate polyurethane and can be produced by dissolving polycarbonate-polyurethane in a suitable solvent, such as hexafluoro isopropanol (HFIP) that is spun and dried.

Figure 14:
FIG. 14 is a (Scanning Electron Microscopy) SEM photomicrograph of an outer surface region of an embodiment of the synthetic scaffold as disclosed herein showing cellular growth after seven days of bioreaction taken at 5000×.
Figure 15:
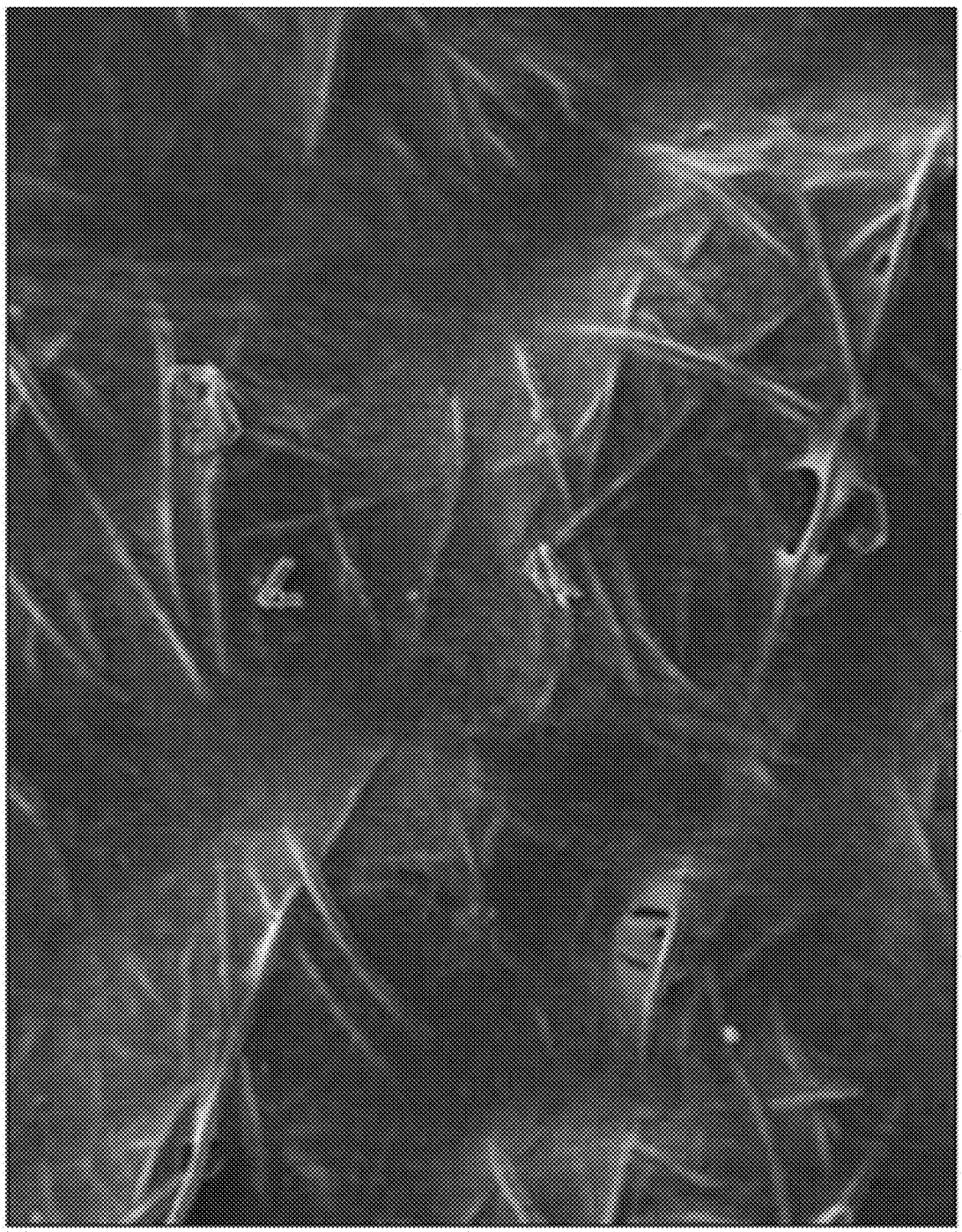
FIG. 15 is a photomicrograph of an outer surface region of an embodiment of the synthetic scaffold as disclosed herein showing cellular growth after seven days of bioreaction.

The spacing and porosity of the electrospun fiber material can be that such that cells seeded on the scaffold surface can adhere in suspended overlying relationship between respective fibers to permit the seeded cellular material to form sheets thereon as illustrated in FIGS. 14 and 15.

Layering of Synthetic Scaffolds

Aspects of the disclosure relate to methods for producing synthetic scaffolds. In some embodiments, tubular synthetic scaffolds (e.g., a synthetic bronchus scaffold) are produced on a mandrel (e.g., by depositing material via electrospraying and/or electrospinning).

In some embodiments, one or more layers of a synthetic scaffold provide structural support to the scaffold, conferring a desired mechanical property to the scaffold. In some embodiments, a braided material (e.g., a braided tube, for example a nitinol braid, a PET braid, or a braid of other metallic or non-metallic material) can be inserted between two different layers of a scaffold to provide structural support. The compression force of the braided material (e.g., the force that the braid can exert on the next layer of material, for example the outer electrospun layer of material) can be controlled by controlling the pick count of the braid. In some embodiments, a braid can be coated (e.g., by dipping or other technique) in an organic solvent to help attach it to one or more other layers of the scaffold 10. In some embodiments, the length of the braid 20 does not extend to the ends of the scaffold body 12. In some embodiments, one or both ends of the scaffold 10 include two or more layers of material without a braided layer, whereas the central portion 28 of the scaffold body 12 includes an additional braided layer.

In some embodiments, one or more layers of a synthetic scaffold provide a barrier in the scaffold, creating a separation (e.g., a relatively impermeable separation) between an inner space (e.g., a luminal space) and an external space. In some embodiments, a barrier can be an electrosprayed polyurethane (PU) layer.

In some embodiments, different layers of a scaffold 10 can include one or more polymers (e.g., polyethylene terephthalate (PET), PU, or blends thereof). In some embodiments, a scaffold 10 can include a nitinol braid sandwiched between an inner PU layer (e.g., that was electrosprayed or electrospun onto a mandrel) and an outer PU layer (e.g., that was electrosprayed onto the braided material).

In certain embodiments the scaffold 10 can be formed using a scaffold support or mandrel. In some embodiments, a scaffold support or mandrel may be coated with a material (e.g., poly(lactic-co-glycolic acid) (PLGA) or other polymer) prior to depositing one or more layers of PU, PET, or a combination thereof.

In certain embodiments, the material in the braid or mesh layer can be composed of absorbable polymeric material. Absorbable polymeric material can include materials that are dissolvable, diffusible, or both.

Scaffold Production-Fiber Materials

In some embodiments, one or more layers of a scaffold may be constructed from fibrous material. In some embodiments, scaffolds comprise one or more types of fiber (e.g., nanofibers). In some embodiments, scaffolds comprise one or more natural fibers, one or more synthetic fibers, one or more polymers, or any combination thereof. It should be appreciated that different material (e.g., different fibers) can be used in methods and compositions described herein. In some embodiments, the material is biocompatible so that it can support cell growth. In some embodiments, the material is permanent, semi-permanent (e.g., it persists for several years after implantation into the host), or rapidly degradable (e.g., it is resorbed within several weeks or months after implantation into the host).

In some embodiments, the scaffold includes electrospun material (e.g., macro or nanofibers). In some embodiments, the electrospun material includes PET (polyethylene terephthalate (sometimes written poly(ethylene terephthalate)). In some embodiments, the electrospun material includes polyurethane (PU). In some embodiments, the electrospun material includes PET and PU.

In some embodiments, the artificial scaffold may include one or more of any of the following materials: elastic polymers (e.g., one or more polyurethanes (PU), for example polycarbonates and/or polyesters), acrylamide polymers, Nylon, resorbable polysulfone polymers, and mixtures thereof. In some embodiments, the scaffold may include polyethylene, polypropylene, poly(vinyl chloride), polymethylmethacrylate (and other acrylic resins), polystyrene, copolymers thereof (including ABA type block copolymers), poly(vinylidene fluoride), poly(vinylidene chloride), and polyvinyl alcohol in various degrees of hydrolysis (e.g., 87% to 99.5%) in cross-linked and non-cross-linked forms. In certain embodiments, the polymeric compound can also include compounds or processes to increase the hydrophilic nature of the polymer. In certain embodiments, this can involve incorporating compounds, such as block copolymers, based on ethylene oxide and propylene oxide. It is also contemplated that the hydrophilic nature of the polymer can be increase by suitable plasma treatment if desired or required.

In some embodiments, the scaffold may include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylate, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun and combined with any other material disclosed herein to produce a scaffold. In some embodiments, highly crystalline polymers like polyethylene and polypropylene may be solution spun or combined with any other material disclosed herein to produce a scaffold.

In some embodiments, one or more polymers are modified to reduce their hydrophobicity and/or increase their hydrophilicity after the scaffold synthesis, but before scaffold cellularization and/or implantation.

The electrospun fibers can have a diameter less than 10 micrometers in certain embodiments. In certain embodiments, the electrospun fibers. In certain embodiments, the electrospun fibers can have a diameter between 3 and 10 micrometers. The electrospun fibers can have a diameter between 3 and 5 micrometers in certain embodiments.

In certain embodiments, it is contemplated that the material in the braid layer can be made in whole or in part of bioabsorbable materials, such as PLGA and the like. It is also contemplated that, in certain configurations, the braid material can be loaded materials and compounds that can promote and/or support tissue growth and regeneration. Non-limiting examples of such compounds and materials include one or more of the following: antibiotics, growth factors and the like.

Electrospinning

In some embodiments, scaffolds are produced that include one or more layers (e.g., of PU and/or PET) produced via electrospinning. Electrospun material can be used for a variety of applications, including as a scaffold for tissue engineering. Appropriate methods of electrospinning polymers may include those described in Doshi and Reneker. Electrospinning process and application of electrospun fibers. J Electrostat. 1995; 35:151-60; Reneker D H, Chun I. Nanometer diameter fibers of polymer produced by electrospinning. Nanotechnology. 1996; 7:216-23; Dzenis Y. Spinning continuous fibers for nanotechnology. Science. 2004; 304:1917-19; or Vasita and Katti. Nanofibers and their applications in tissue engineering. Int J. Nanomedicine. 2006; 1(1): 15-30, the contents of which relating to electrospinning are incorporated herein by reference. Electrospinning is a versatile technique that can be used to produce either randomly oriented or aligned fibers with essentially any chemistry and diameters ranging from nm scale (e.g., around 15 nm) to micron scale (e.g., around 10 microns).

In some embodiments, electrospinning and electrospraying techniques used herein involve using a high voltage electric field to charge a polymer solution (or melt) that is delivered through a nozzle (e.g., as a jet of polymer solution) and deposited on a target surface. The target surface can be the surface of a static plate, a rotating drum (e.g., mandrel), or other form of collector surface that is both electrically conductive and electrically grounded so that the charged polymer solution is drawn towards the surface.

In some embodiments, the electric field employed is typically on the order of several kV, and the distance between the nozzle and the target surface is usually several cm or more. The solvent of the polymer solution evaporates (at least partially) between leaving the nozzle and reaching the target surface. This results in the deposition of polymer fibers on the surface. Typical fiber diameters range from several nanometers to several microns. The relative orientation of the fibers can be affected by the movement of the target surface relative to the nozzle. For example, if the target surface is the surface of a rotating mandrel, the fibers will align (at least partially) on the surface of the mandrel in the direction of rotation. In some cases, the nozzle can be scanned back and forth between both ends of a rotating mandrel.

In some embodiments, the size and density of the polymer fibers, the extent of fiber alignment, and other physical characteristics of an electrospun material can be impacted by factors including, but not limited to, the nature of the polymer solution, the size of the nozzle, the electrical field, the distance between the nozzle and the target surface, the properties of the target surface, the relative movement (e.g., distance and/or speed) between the nozzle and the target surface, and other factors that can affect solvent evaporation and polymer deposition.

Electrospinning and electrospraying processes may be used for producing interlinked polymer fiber scaffolds (e.g., hollow synthetic scaffolds) on a mandrel.

Support/Mandrel

In some embodiments, scaffold 10 (e.g., a scaffold having two or more layers) can be produced using a support (e.g., a solid or hollow support) on which the scaffold 10 can be formed. For example, a support can be an electrospinning collector, for example a mandrel, or a tube, or any other shaped support. It should be appreciated that the support can have any size or shape. However, in some embodiments, the size and shape of the support is designed to produce a scaffold that will support an artificial tissue of the same or similar size as the bronchus tissue (or portion thereof) being replaced or supplemented in a host. It should be appreciated that a mandrel for electrospinning should have a conductive surface. In some embodiments, an electrospinning mandrel is made of a conductive material (e.g., including one or more metals). However, in some embodiments, an electrospinning mandrel includes a conductive coating (e.g., including one or more metals) covering a non-conductive central support.

It has been found that positioning suitable braid material to be integrated in the resulting scaffold 10 at a location proximate to the surface of the mandrel can serve as an aid to facilitate removal of the resulting scaffold 10 from contact with the mandrel.

Scaffold Properties

It should be appreciated that aspects of the disclosure are useful for enhancing the physical and functional properties of any scaffold, and for example, a scaffold based on electrospun and/or electro sprayed fibers. In some embodiments, one or more scaffold components can be thin sheets, cylinders, thick ribs, solid blocks, branched networks, etc., or any combination thereof having different dimensions. In some embodiments, the dimensions of a complete and/or assembled scaffold are similar or identical to the dimension of a tissue or organ being replaced. In some embodiments, individual components or layers of a scaffold have smaller dimensions. For example, the nanofiber layers having a thickness of 1 nm or more, 10 nm or more, 100 nm or more, 500 nm or more, or 900 nm or more. The nanofiber layer having a thickness of 1 micron or more, 10 microns or more, 100 microns or more, or 500 microns or more. The nanofiber layers having a thickness of 10 mm or less, 5 mm or less, 1 mm or less, or 800 microns or less. However, in some embodiments, the dimensions of one or more scaffold components can be from about 1 mm to 50 cm. However, larger, smaller, or intermediate sized structures may be made as described herein.

In some embodiments, scaffolds are formed as tubular structures that can be seeded with cells to form tubular tissue regions such as the bronchus. It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches. In some embodiments, a tubular scaffold is produced having an opening at one end, both ends, or a plurality of ends (e.g., in the case of a branched scaffold). However, a tubular scaffold may be closed at one, both, or all ends, as aspects of the invention are not limited in this respect. It also should be appreciated that aspects of the invention may be used to produce scaffolds for any type or organ, including hollow and solid organs, as the invention is not limited in this respect. In some embodiments, aspects of the invention are useful to enhance the stability of scaffold or other structures that include two or more regions or layers of fibers (e.g., electrospun nanofibers) that are not physically connected.

In some embodiments, a scaffold is designed to have a porous surface having pores ranging from around 10 nm to about 100 microns in diameter that can promote cellularization. In some embodiments, pores have an average diameter of less than 50 microns, less than 40 microns, less than 30 microns, less than 20 microns or less than 10 microns (e.g., approximately 5, approximately 10, or approximately 15 microns). In some embodiments, pores have an average diameter of 20-40 microns. In some embodiments, pore size is selected to prevent or reduce an immune response or other unwanted host response in the subject. Pore sizes can be estimated using computational and/or experimental techniques (e.g., using porosimetry). However, it should be appreciated that pores of other sizes also can be included.

In some embodiments, a surface layer of a scaffold is synthesized using fibers that include one or more dissolvable particles that can be dissolved during or after synthesis (e.g., by exposure to a solvent, an aqueous solution, for example, water, or a buffer) to leave behind pores the size of the dissolvable particles. In some embodiments, the particles are included in the polymer mix that is pumped to the nozzle of an electrospinning device. As a result, the particles are deposited along with the fibers. In some embodiments, the electrospinning procedure is configured to deposit thick fibers (e.g., having an average diameter of several microns, about 10 microns, and thicker). In some embodiments, if the fibers are deposited in a dense pattern, one or more fibers will merge prior to curing to form larger macrostructures (e.g., 10-100 microns thick or more). In some embodiments, these macrostructures can entangle two or more layers of fibers and or portions (e.g., fibers) from two or more different components of a scaffold thereby increasing the mechanical integrity of the scaffold. In some embodiments, when such macrostructures are formed (e.g., via electrospinning as described herein) at one or more stages during scaffold synthesis (e.g., to connect two or more layers and/or components), the surface of the macrostructure(s) can be treated (e.g., etched or made porous using dissolvable particles as described herein) in order to provide a surface suitable for cellularization.

In some embodiments, the amount of flexible scaffold material (e.g., the slack) between two or more structural components (e.g., rings), between structural members (e.g., arcuate members) of a single continuous structural component, and/or of a braided support material can be used to determine the mechanical properties (e.g., tensile strength, elongation, rotation, compression, range of motion, bending, resistance, compliance, degrees of freedom, elasticity, or any other mechanical property, or a combination thereof) of a synthetic scaffold.

In certain embodiments, the scaffold 10 can also include a cellular sheath derived from cells seeded on the outer surface of the scaffold during incubation. The cellular sheath adheres to and is in overlying relationship to the outer surface of the scaffold. It is contemplated that a major portion of the cells present in the cellular sheath will be connected to the outermost surface of the outer surface and will span pores defined therein to form a continuous or generally continuous surface.

In certain embodiments, the cellular sheath can have a thickness sufficient to provide structural integrity to the sheath layer. In certain embodiments, the cellular sheath will be composed of a number of cells which are in contact with the external surface of the scaffold sufficient to direct regenerating cells in contact with the sheath to produce a tissue wall that overlays the sheath but does not integrate therewith. In certain embodiments, the sheath can be composed of a lining that is between 1 and 100 cells thick on average. Certain embodiments can have a cell thickness between 10 and 100; between 10 and 30; between 20 and 30, between 20 and 40; between 20 and 50; between 10 and 20; between 30 and 50; between 30 and 60; between 40 and 60; between 40 and 70; between 70 and 90.

The scaffold 10 with the associated cellular sheath provides a moveable insertable device that can be positioned in a suitable bronchus resection site. The scaffold 10 with the associated cellular sheath in contact therewith can be transported to the desired resection site for implantation. In certain embodiments, the scaffold 10 is configured to be removable from the implantation site after suitable regeneration of the resected organ. In certain embodiments, the removed scaffold will include some or all of the cellular sheath connected thereto.

Also disclosed are various embodiments of method of regenerating a tubular organ, such as a bronchus. In certain embodiments, the method 100 includes the step of resecting a that comprises resecting a portion of a tubular organ in a subject as at reference numeral 110. The organ to be resected can be a tubular organ such as a bronchus that has been damaged or compromised by disease injury, trauma or congenital conditions. In certain embodiments, non-limiting examples of suitable organs include one of the bronchi or the like.

The resection can be achieved by any suitable surgical procedure and produced a resected organ portion that remains connected to the bronchus and remains in the subject after resection. The resection operation can yield suitable resection edges in certain embodiments.

After resection is completed, a synthetic scaffold is implanted at the site of the resection as at reference numeral 120. In certain embodiments, implantation can include the step of connecting the respective ends of the resected organ as it remains in the subject to respective ends of the synthetic scaffold such that the synthetic scaffold and at the resected organ can achieve a suitable junction between the respective members. This can be achieved by one or more of sutures, bioorganic tissue glue, etc.

In certain embodiments, the synthetic scaffold that is implanted can be a tubular member that has an outer polymeric surface and a cellularized sheath layer overlying at least a portion of the of the outer polymeric surface. Various embodiments of the synthetic scaffold have been discussed and can be employed and utilized in the method disclosed herein. In certain embodiments, the synthetic scaffold will include a first end and a second end opposed to the first end, an outer polymeric surface positioned between the first end and the second end and a cellularized sheath layer overlying at least a portion of the outer polymeric surface. In certain embodiments, the implantation step can be one that brings at least a portion of the cellularized sheath layer into proximate contact with at least one of the resection edges of the resected organ portion.

In certain embodiments, the method as disclosed herein also includes the step of maintaining the synthetic scaffold at the resection site for a period of time sufficient to achieve guided tissue growth along the synthetic scaffold as at reference numeral 130. In certain embodiments, the guided tissue growth is derived from and is in contact with the tissue present in the resected organ portion remaining in the subject. In certain embodiments, the guided tissue growth will be contiguous with the associated regions of the resected organ. In certain embodiments, the guided tissue growth will exhibit differentiated tissue. In certain embodiments, the guided tissue growth will parallel the outer surface of the cellularized sheath layer at a position outward thereof. In certain embodiments, the guided tissue growth is derived from and is in contact with the tissue present in the resected organ portion remaining in the subject and will be contiguous with the associated regions of the resected organ. The guided tissue growth will exhibit differentiated tissue growth and can be parallel the outer surface of the cellularized sheath layer at a position outward thereof.

After the guided tissue growth has been achieved, the process 100 as disclosed herein can include step of removing the synthetic scaffold as at reference numeral 140. In certain embodiments, the removing step occurs in a manner such that the guided tissue growth remains in the contact with the resected portion of the organ remaining in the subject. In certain embodiments, the removal process can include intrascopically removing the synthetic scaffold from the interior of the guided tissue growth.

In certain embodiments, the synthetic scaffold can be constructed in whole or in part from bioabsorbable polymeric material. In such situations, the method as disclosed herein can include the step of maintaining contact between the synthetic scaffold and the resection edge for intervals sufficient to achieve guided tissue growth along the synthetic scaffold such that at least a portion of the synthetic scaffold is absorbed at the site of resection within a period of time sufficient to achieve guided tissue growth along the synthetic scaffold. In certain embodiments where the scaffold is composed entirely of bioabsorbable material, the scaffold will be configured to maintain structural integrity during guided tissue growth. In certain embodiments, where the synthetic scaffold is composed of bioabsorbable material in selected regions, it is contemplated that the remainder of the scaffold can be removed by suitable procedures after the guided tissue growth has been achieved.

Guided tissue growth can be monitored by suitable means. In certain embodiments, tissue growth can be monitored endoscopically.

In certain embodiments of the method as disclosed herein, the method can also include the step of imparting cellular material onto the polymeric surface of the synthetic scaffold and allowing the cellular material to grow to form the cellular sheath layer, the imparting and allowing steps occurring prior to the resecting step.

In certain embodiments, the synthetic scaffold that is employed in the method disclosed herein a tubular member where the outer surface includes spun polymeric fibers. In certain embodiments, the spun fibers can be electrospun by suitable methods, such as those described in this disclosure. In certain embodiments, the cellularized sheath layer spans at least a portion outwardly positioned electrospun fibers. The cellularized sheath layer can be composed of cellular material, the cellular material including at least one of mesenchymal cells, stem cells, pluripotent cells. The cellular material can be autologously derived from the subject or can be allogenically derived.

Without being bound to any theory, it is believed that implanting a synthetic scaffold, such as those as variously disclosed herein, particularly one seeded with an overlying cellular sheath, promotes growth, regeneration and differentiation of the subject tissue in contact with or proximate to the location of the implanted synthetic scaffold. The growing regenerating tissue is guided by the synthetic scaffold and associated sheath to produce a tubular cellular body that is integrally connected to the resected ends of the remaining tubular organ and outwardly flaring to encapsulate the synthetic scaffold and associated cellular sheath layer. It is believed that the scaffold and associated cellular sheath layer may promote or stimulate regenerative growth of the resected tissue while minimizing tissue rejection responses. It is also believed that the presence of the cellular sheath layer can reduce or minimize penetration of the regenerated tissue into the sheath layer during growth and differentiation. In certain embodiments, tissue generation proceeds from the respective ends toward the middle. Once the regenerated tissue is in position, the synthetic scaffold can be removed. In certain embodiments, immediately after the removal of the synthetic scaffold, the regenerated tissue structure will lack the inner epithelial layer.

This layer has been seen to regenerate after removal of the scaffold as illustrated in FIGS. 11A, 11B, and 11C taken immediately after scaffold removal, 2 months post removal and 3 months post removal respectively.

In order to further understand the present disclosure, reference is made to the following Examples. These Examples are included for purposes of illustration and are to be considered illustrative of the present disclosure and the invention as set forth in the claims.

Examples

A synthetic bronchial substitute is made of polyurethane material through electrospinning process followed by surface plasma treatment employing the process outlined in FIG. 1 including adipose biopsy, scaffold electrospinning, seeding, surgical implantation, and associated characterizations.

In the process employed, an electrospun polyurethane scaffold was treated by Ethylene/02 plasma and seeded with autologous aMSCs isolated from the subject pig. The seeded scaffold was then implanted into the pig (38-025) to replace a 2 cm section of left main bronchus.

The scaffold employed was then seeded with autologous aMSCs isolated from a Yucatan mini-pig. A section of the left main bronchus was resected from the pig during the sleeve lobectomy and the seeded scaffold was surgically implanted using end-to-end anastomosis technique. The polyurethane scaffold was removed a few weeks later through bronchoscopy and the bronchial defect was bridged by newly regenerated tissue. A bronchial stent was deployed to support the following tissue regeneration as needed.

Figure 2:
FIG. 2 is a Day 8 bronchoscopy image of a resected region according to the method outlined in FIG. 1.
Figure 3:
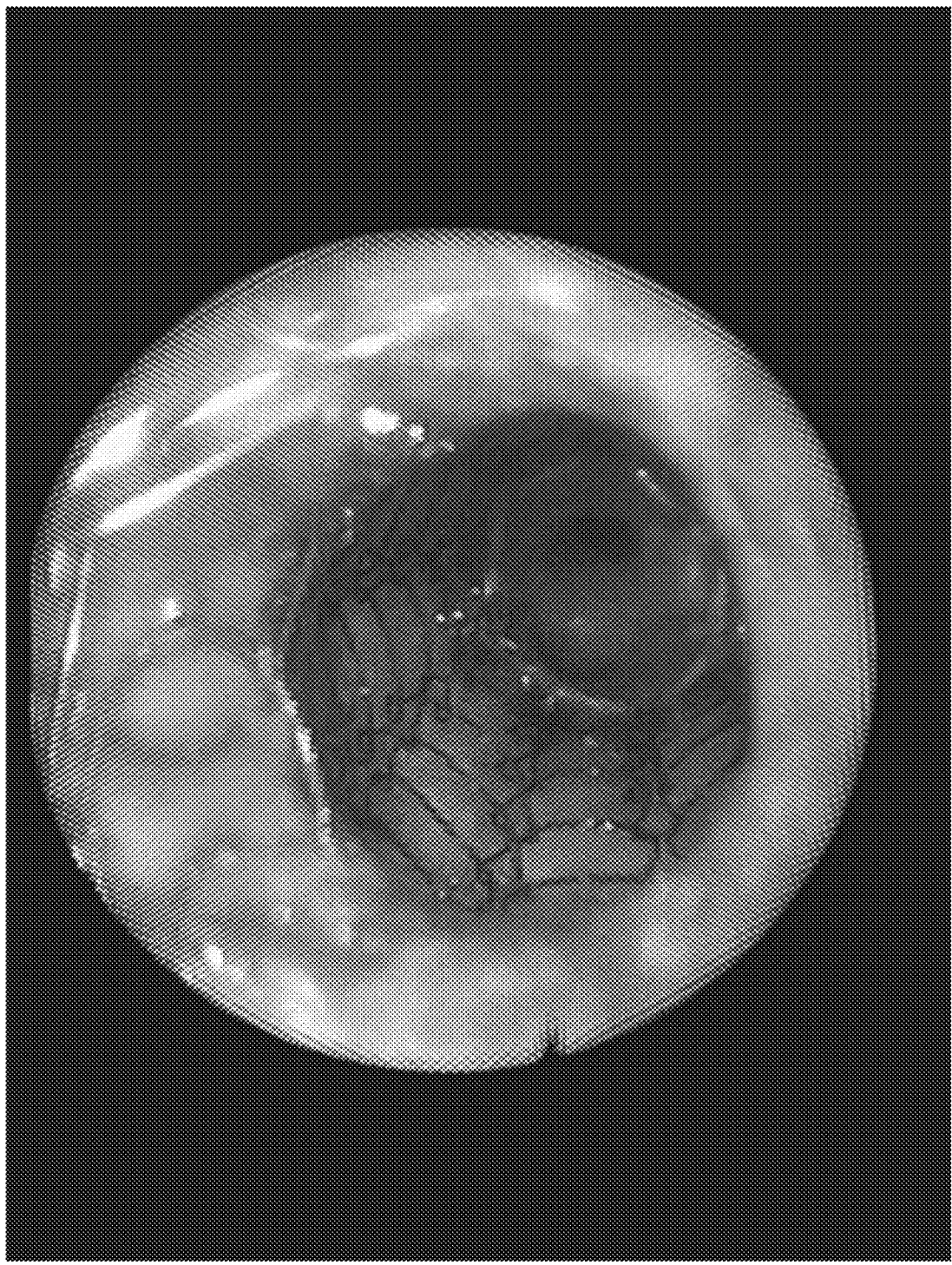
FIG. 3 is a Day 8 bronchoscopy image of a resected region according to the method outlined in FIG. 1.

The test subject animal survived the implantation procedure and did well for its entire 613-days in-life time. Tissue growth of the bronchus was monitored by a series of bronchoscopy assessments. Representative images of bronchoscopy at specific intervals. Images taken during the bronchoscopy at Day 8 confirm that the anastomosis was intact, and the airway is clean. Images are presented in FIGS. 2 and 3.

Figure 4:
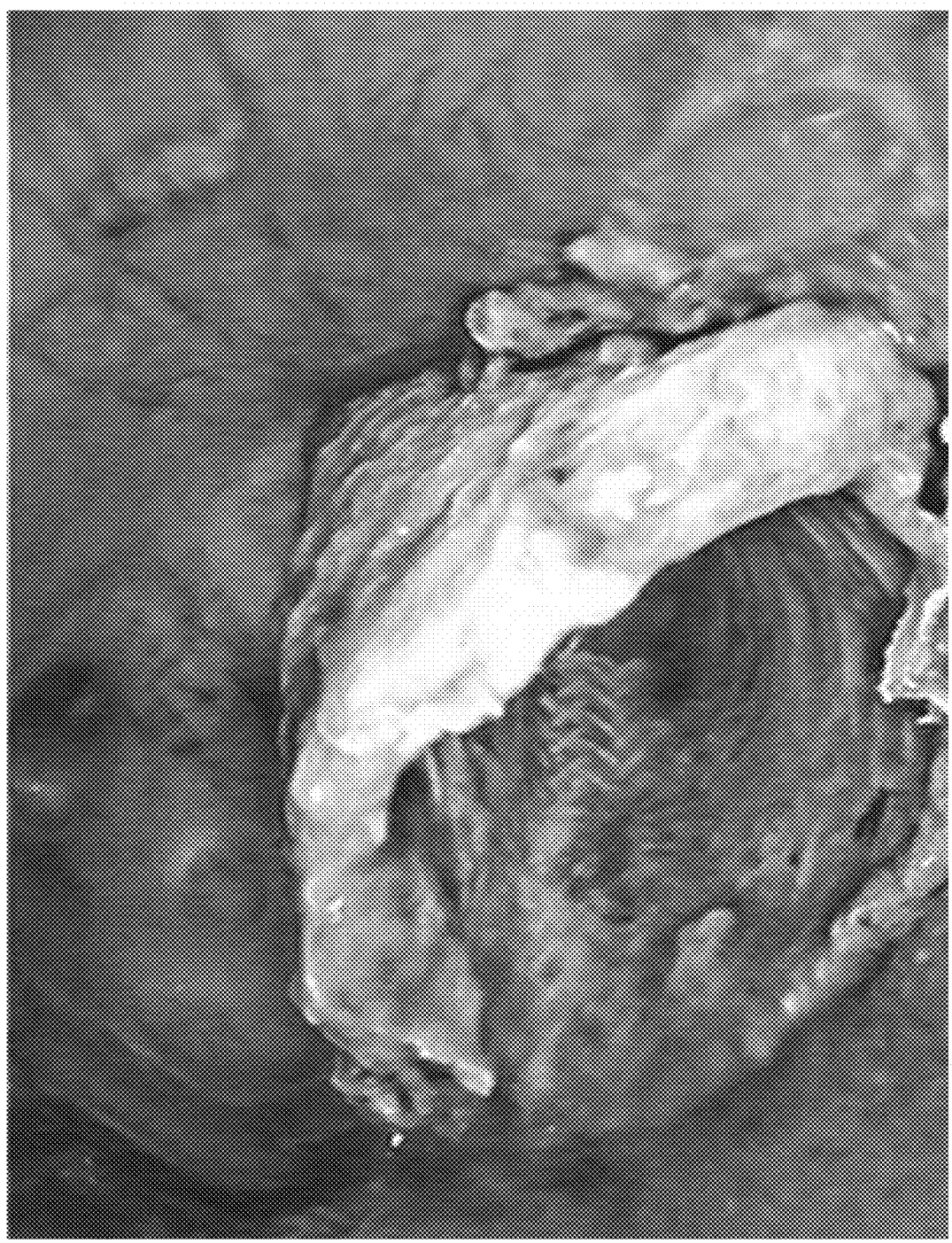
FIG. 4 is a Day 69 bronchoscopy image of a resected region according to the method outlined in FIG. 1.
Figure 5:
FIG. 5 is a Day 69 inspection of a scaffold removed from a test subject.

Bronchoscopy at Day 69 indicated that the scaffold remained intact. Sutures at the distal and proximate ends were cut and the scaffold structure analyzed. The 2 cm of bronchial defect was covered by newly formed tissues. Images are depicted in FIGS. 4 and 5.

Figure 6:
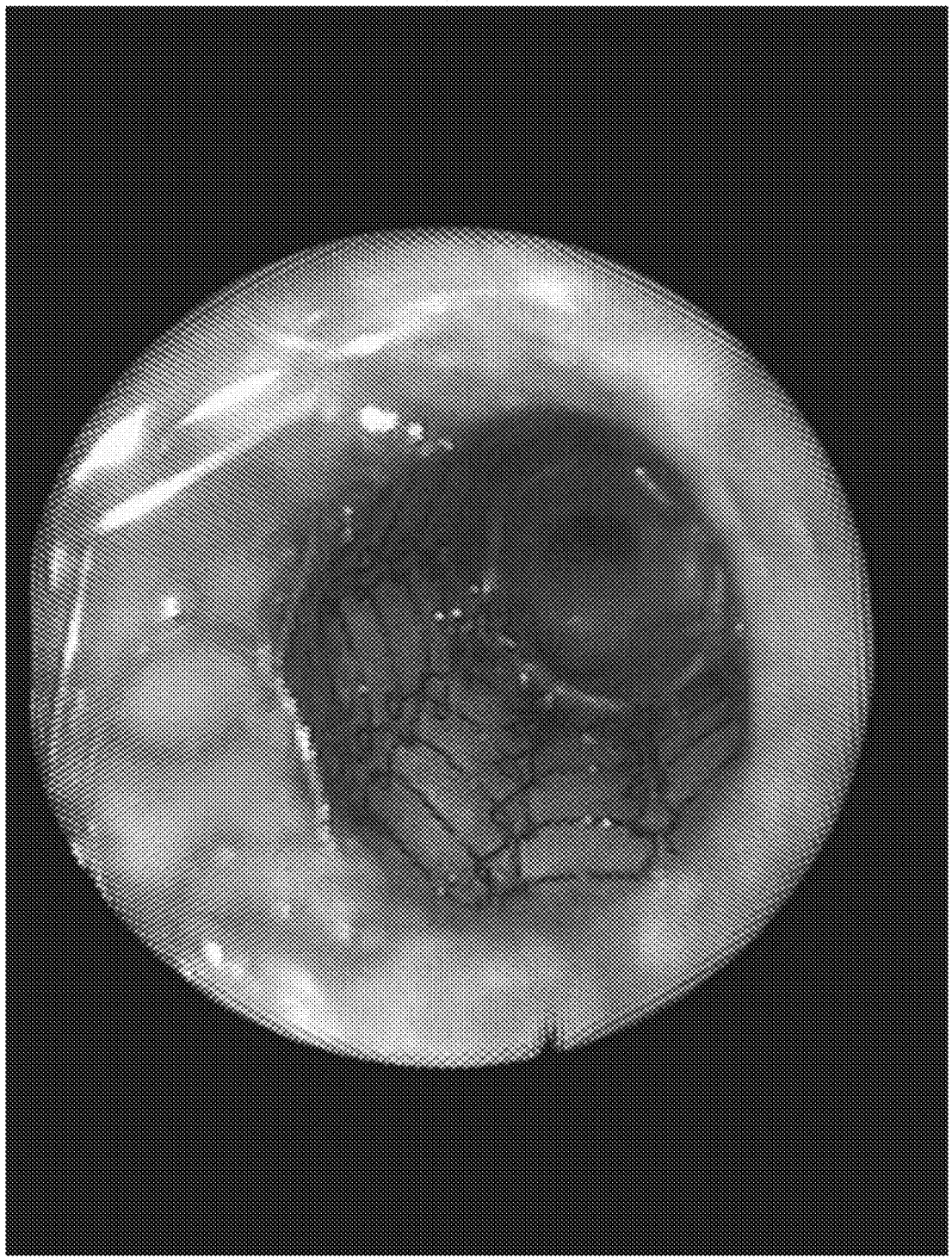
FIG. 6 is an image of a post-scaffold removal Day 76 bronchoscopy of a resected region according to the method outlined in FIG. 1.
Figure 7:
FIG. 7 is an image of a post-scaffold removal Day 76 bronchoscopy image of a resected region according to the method outlined in FIG. 1.

A day 76 Bronchoscopy at Day 76 includes insertion of a stenotic-placed tracheobronchial stent to open the airway to 4.5 mm. Inspection indicated that an intact epithelium layer with some reddening apparent. Images are depicted at FIGS. 6 and 7.

Figure 8:
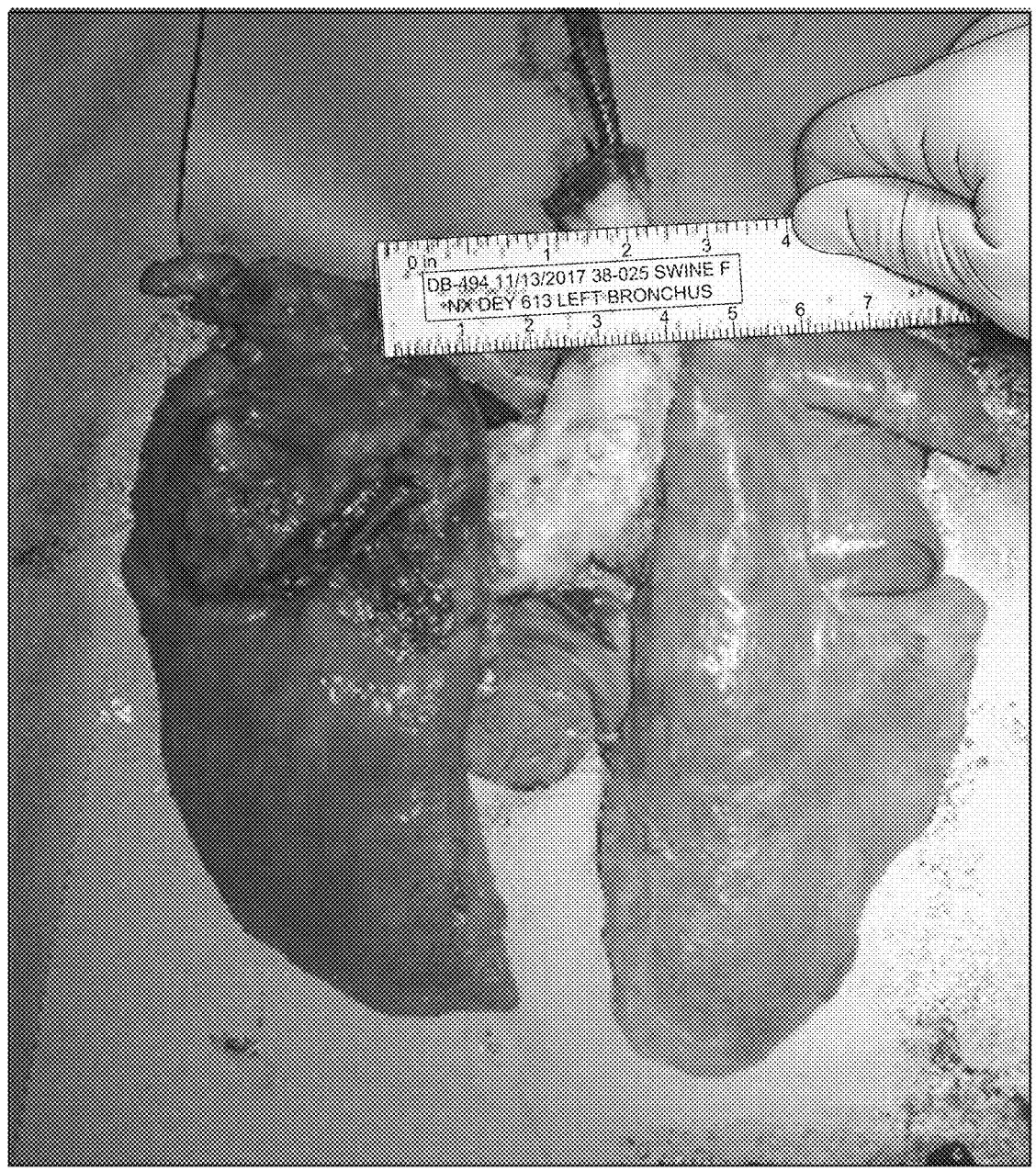
FIG. 8 is an image of the removed tracheal and surrounding lungs.
Figure 9:
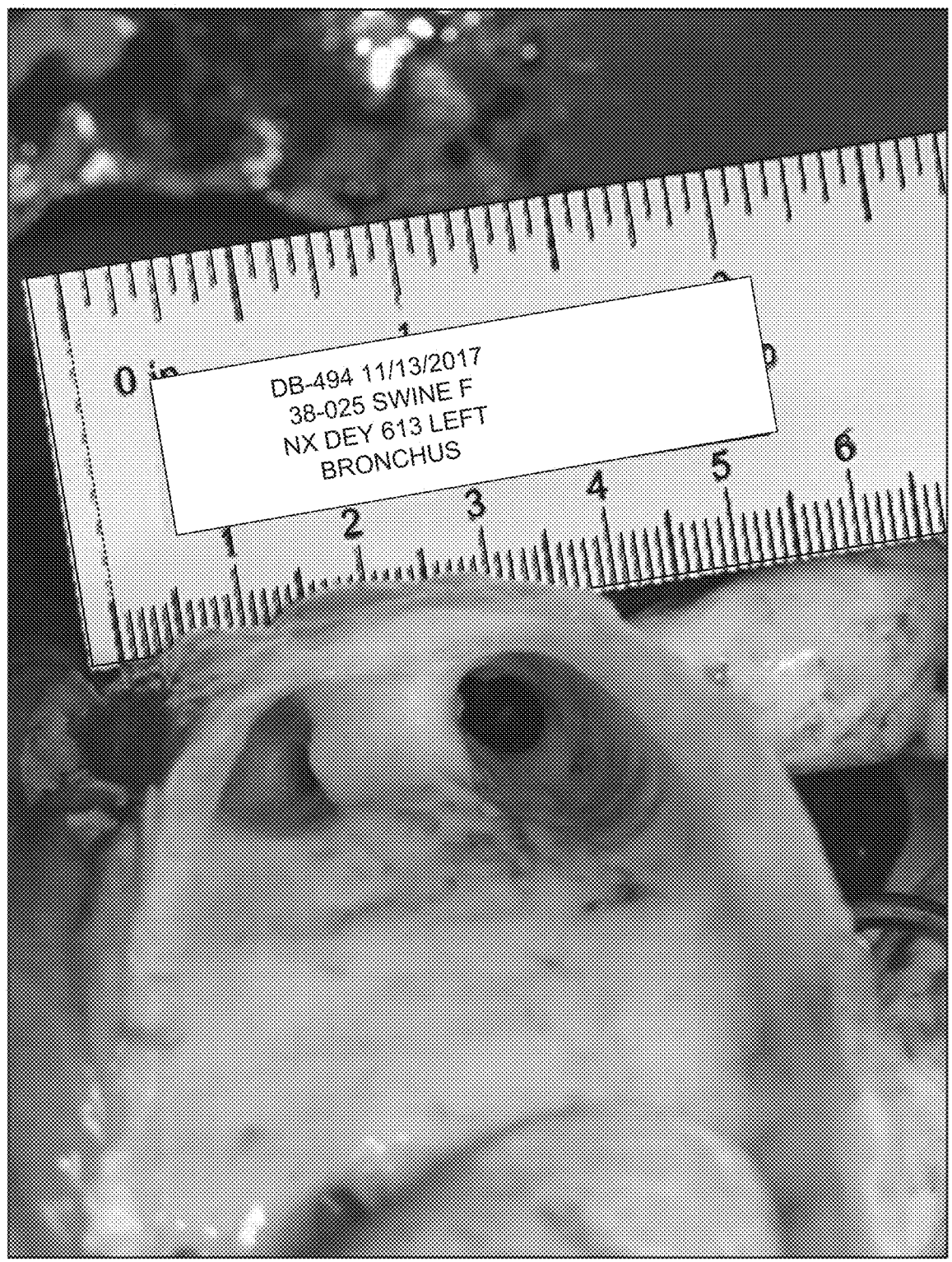
FIG. 9 is an image of a post-scaffold removal Day 76 bronchoscopy image.
Figure 10:
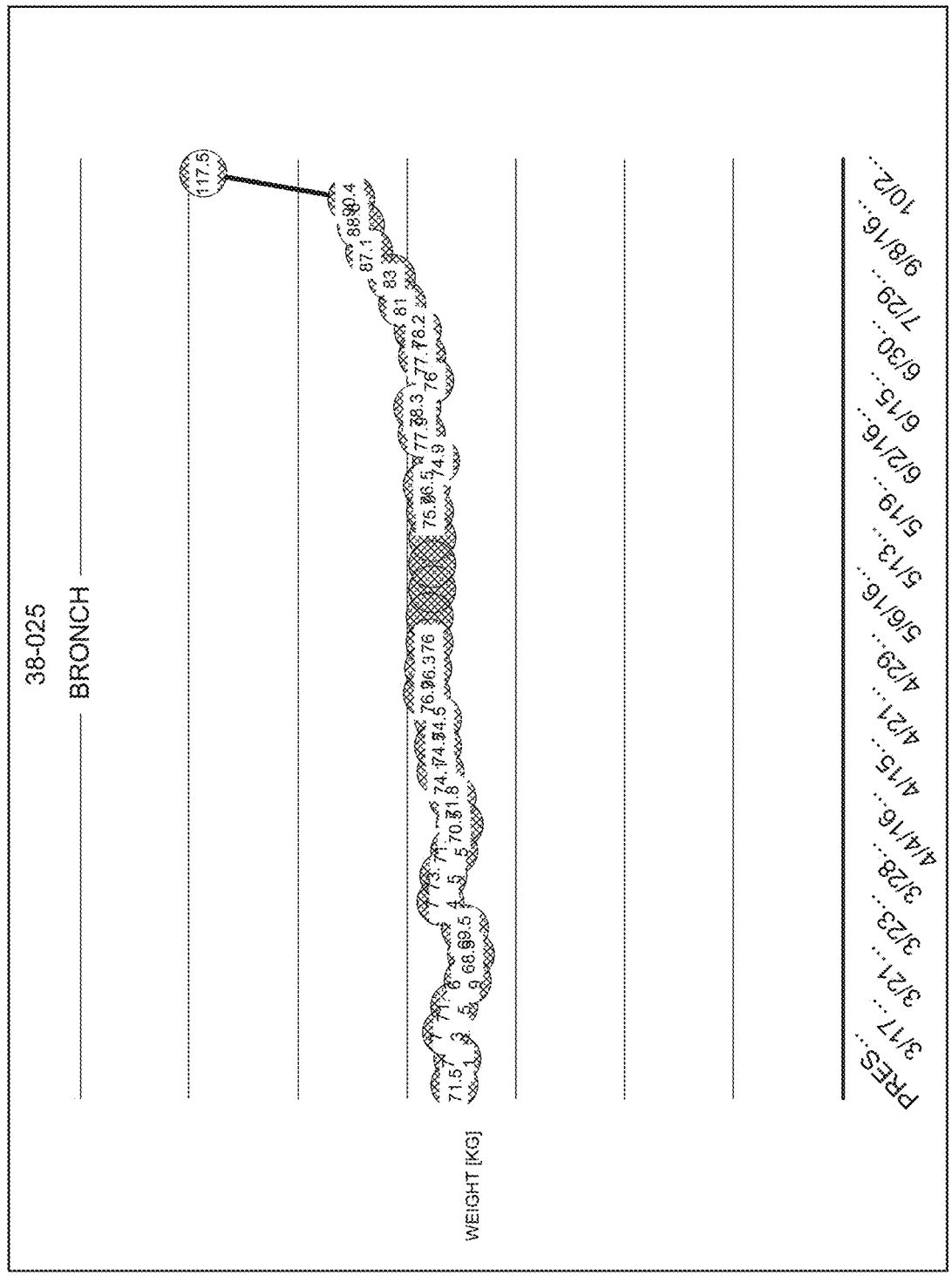
FIG. 10 is graph outlining weight change of test animal post bronchial surgery.

Necropsy and Bronchial Explanation:

Left lung lobe adhered to thoracic wall-moderate strength. Removed entire trachea and lungs and dissected down to left bronchus at Day 613. The regenerative area and surrounding tissues were explanted, sectioned and preserved in 10% NBF. Images are presented at FIGS. 8 and 9.

The test animal showed a normal growth pattern and gained significant weight on a maintenance diet. All animals were maintained under the care of the Attending Veterinarian.

In summary, the preliminary animal study shown that the novel aMSCs seeded polyurethane scaffold supported the bronchial tissue regeneration and was removable/retrievable after the bronchial defect was bridged by newly formed tissues. The elective use of such a bronchial substitute would be a secure adjunct to the surgical arsenal and would contribute to a reduction in the pneumonectomy rate and of local recurrences associated with sleeve bronchial resections.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A synthetic scaffold comprising:
   a body section, the body section having a first end, a second end opposed to the first end, and a middle section extending between the first end and the second end, the body section further having a least one portion configured as a tubular member, the body section comprising an outwardly oriented surface, the outwardly oriented surface having at least one region composed of spun polymeric fibers, the spun polymeric fibers having an average fiber diameter between 15 nm and 10 microns, at least a portion of the spun polymeric fibers interlinked to form pores having an average diameter less than 50 microns, the pores defining at least one porous region present on the outwardly oriented surface; and
   at least one colonized cell line adhering to the porous region defined on the outwardly oriented face of the body section,
   wherein at least one portion of the middle section of the body section is configured to bridge a first portion and a second portion of resected edges of a tubular organ,
   wherein the spun polymeric fibers are electrospun, interconnected, and form an outer layer of the body section and at least one inner layer, the outer layer in overlying contact with the at least one inner layer, and the outer layer and the at least one inner layer being fused so that the spun polymeric fibers of the outer layer and the at least one inner layer propagate cells of the at least one colonized cell line and diffuses the cells from the spun polymeric fiber to the resected edges of the tubular organ.

2. The synthetic scaffold of claim 1, wherein the electrospun material has an average fiber diameter of 3 to 10 micrometers and is composed of at least one of the following polymeric materials: polyvinylidene fluoride, syndiotactic polystyrene, copolymer of vinylidene fluoride and hexafluoropropylene, polyvinyl alcohol, polyvinyl acetate, poly (acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly (methyl methacrylate), polyethylene terephthalate, and polyurethane.

3. The synthetic scaffold of claim 1, wherein at least one layer is a polymeric material containing polyethylene terephthalate, polyurethane, blends of polyethylene terephthalate and polyurethane.

4. The synthetic scaffold of claim 1, wherein the polymeric braided support material is composed of at least one of polyethylene terephthalate, polyurethane, nitinol braid sandwiched between two or more polyurethane layers, and mixtures thereof.

5. The synthetic scaffold of claim 1, wherein the at least one colonized cell line adheres to the outwardly oriented surface of the body section as a plurality of discrete cell colonies and wherein the at least one colonized cell line is composed of cellular material, the cellular material composed of mesenchymal cells and stem cells.

6. The synthetic scaffold of claim 1, wherein the at least one colonized cell line adheres to the outwardly oriented surface of the body section and comprises at least one sheath, the at least one sheath axially disposed on the outwardly oriented surface composed of cellular material, the cellular material composed of mesenchymal cells and stem cells present in a defined layer the defined layer being between 1 and 100 celled thick.

7. The synthetic scaffold of claim 1, wherein the sheath layer of cellular material overlays and adheres to the electrospun fibers present on the outer surface such that the cellular material, is contained on the outer surface and spans the pores defined therein.

8. The synthetic scaffold of claim 1, further comprising at least one hole, indent, protrusion, or a combination thereof defined within a surface of at least one of the first or second ends that is adapted to assist in the retrieval of the scaffold from a subject after tissue regeneration has occurred around the scaffold at the site of implantation in the subject.

9. A method for regenerating tissue at a region of trauma defined in a tubular organ in the respiratory system of a subject, the method comprising the steps of:
  resecting a portion of the tubular organ in a subject at a resection site, the resection step producing a resected organ portion and at least one native organ wall;
  removing the resected organ portion having the region of trauma from the resection site so that the at least one native organ wall is free of contact with the resected organ portion and so that an open portion of the tubular organ is defined at the resection site;
  implanting a synthetic scaffold within the tubular organ at the site of resection site, the synthetic scaffold including an outer polymeric surface and at least one colonized cell line adhering to the outer polymeric surface of the synthetic scaffold, the at least one colonized cell line positioned at the open portion;
  maintaining the synthetic scaffold at the open portion of the resection for a time interval sufficient to achieve guided tissue growth along the synthetic scaffold, the guided tissue growth derived from and in contact with the tissue present in the at least one native organ wall; and
  after achieving guided tissue growth, removing the synthetic scaffold from within the tubular organ, the removing the synthetic scaffold from the tubular organ step occurring in a manner such that the guided tissue growth remains in the contact with the at least one native organ wall,
  after removing the synthetic scaffold from the implantation site, inserting a bronchial stent into the tubular organ to support the guided tissue growth; and
  when the guided tissue growth is self-supporting, removing the bronchial stent from tubular organ.

10. The method of claim 9 wherein the at least one colonized cell line is present as a cellularized sheath layer overlying at least a portion of the outer polymeric surface.

11. The method of claim 10 wherein the tubular organ in the respiratory system is the bronchus.

12. The method of claim 11 wherein the synthetic scaffold has an end region and the resected bronchus has at least one resected edge, wherein the synthetic scaffold is implanted such that the end region is proximate to the at least one resected edge of the bronchus.

13. The method of claim 9, wherein the synthetic scaffold comprises an electrospun polyurethane.

14. The method of claim 9, wherein resecting a portion of a tubular organ in a subject includes retaining the at least one native organ wall so that the at least one native organ wall extends from a first end to a second end of the tubular organ.

15. The method of claim 9, wherein the resected organ portion is less than a full circumference of the tubular organ.

16. The method of claim 15, wherein the tubular organ is a bronchus.

17. The method of claim 9, wherein the resected organ portion is a full circumferential portion of the tubular organ.

18. The method of claim 9, wherein resecting a portion of a tubular organ in a subject includes resecting a circumferential portion of the tubular organ so that the open portion extends between at least two native organ walls that are free of connection with each other.

* * * * *